United States Patent
Aujla

(10) Patent No.: US 11,628,009 B2
(45) Date of Patent: Apr. 18, 2023

(54) EP CATHETER WITH TRAINED SUPPORT MEMBER, AND RELATED METHODS

(71) Applicant: BIOSENSE WEBSTER (ISRAEL) LTD., Yokneam (IL)

(72) Inventor: Vishav Manak Singh Aujla, Valencia, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 198 days.

(21) Appl. No.: 14/574,246

(22) Filed: Dec. 17, 2014

(65) Prior Publication Data
US 2016/0175039 A1    Jun. 23, 2016

(51) Int. Cl.
*A61B 18/14*      (2006.01)
*A61M 25/01*      (2006.01)
(Continued)

(52) U.S. Cl.
CPC ..... *A61B 18/1492* (2013.01); *A61M 25/0009* (2013.01); *A61M 25/0158* (2013.01);
(Continued)

(58) Field of Classification Search
CPC ...... A61B 18/1492; A61B 2017/00305; A61B 2017/00318; A61B 2017/00867; A61B 2018/00166; A61B 2018/00357; A61B 2018/00434; A61B 2018/00577; A61B 2017/00331; A61M 25/0158; A61M 2025/0161
See application file for complete search history.

(56) References Cited

U.S. PATENT DOCUMENTS

| 4,758,222 A | 7/1988 | McCoy |
|---|---|---|
| 5,617,854 A | 4/1997 | Munsif |

(Continued)

FOREIGN PATENT DOCUMENTS

| JP | H 03-081572 A | 4/1991 |
|---|---|---|
| JP | H 04-051967 A | 2/1992 |

(Continued)

OTHER PUBLICATIONS

European Search Report for EP Patent Application No. 15200512.0, dated May 24, 2016, 8 pages.

(Continued)

*Primary Examiner* — Joanne M Rodden
*Assistant Examiner* — Sean W Collins
(74) *Attorney, Agent, or Firm* — Lewis Roca Rothgerber Christie LLP

(57) ABSTRACT

A catheter adapted for deflection in a narrow tubular region and/or sharp turn, has an elongated body, a deflection section having a support member adapted for heat activation to assume a trained configuration, and a lead wire configured to deliver a current to the support member for heat activation. The support member is constructed of a shaped memory alloy, for example, nitinol, and the lead wire is adapted to directly heat the support member. Moreover, the catheter may include a thermally insulating layer covering at least a portion of the support member. The trained configuration of the support member extends in a single dimension, in two dimensions or in three dimensions.

20 Claims, 11 Drawing Sheets

(51) Int. Cl.
*A61M 25/00* (2006.01)
*A61B 18/00* (2006.01)
*A61B 17/00* (2006.01)

(52) U.S. Cl.
CPC .............. *A61B 2017/00305* (2013.01); *A61B 2017/00318* (2013.01); *A61B 2017/00526* (2013.01); *A61B 2017/00867* (2013.01); *A61B 2018/00166* (2013.01); *A61B 2018/00357* (2013.01); *A61B 2018/00404* (2013.01); *A61B 2018/00434* (2013.01); *A61B 2018/00511* (2013.01); *A61B 2018/00577* (2013.01); *A61B 2218/002* (2013.01)

(56) References Cited

U.S. PATENT DOCUMENTS

| | | | |
|---|---|---|---|
| 5,964,757 | A | 10/1999 | Ponzi |
| 6,126,654 | A | 10/2000 | Giba et al. |
| 6,652,491 | B1 | 11/2003 | Walker et al. |
| 8,690,884 | B2 | 4/2014 | Linderman et al. |
| 2002/0111618 | A1 | 8/2002 | Stewart et al. |
| 2004/0158143 | A1 | 8/2004 | Flaherty et al. |
| 2005/0006009 | A1* | 1/2005 | Esashi ............... A61M 25/0138 148/518 |
| 2006/0064055 | A1 | 3/2006 | Pile-Spellman et al. |
| 2006/0074403 | A1 | 4/2006 | Rafiee |
| 2006/0241366 | A1* | 10/2006 | Falwell ............... A61B 18/1492 600/374 |
| 2007/0066878 | A1 | 3/2007 | Worley et al. |
| 2009/0088838 | A1* | 4/2009 | Shaolian ............... A61F 2/2448 623/2.37 |
| 2010/0069734 | A1 | 3/2010 | Worley et al. |
| 2010/0268217 | A1 | 10/2010 | Habib |
| 2010/0280449 | A1* | 11/2010 | Alvarez ............... A61B 34/30 604/95.04 |
| 2011/0264011 | A1 | 10/2011 | Wu et al. |
| 2012/0108980 | A1* | 5/2012 | Shilling ............... A61B 8/0883 600/466 |
| 2012/0123258 | A1 | 5/2012 | Willard |
| 2012/0123406 | A1 | 5/2012 | Edmunds et al. |
| 2012/0136350 | A1* | 5/2012 | Goshgarian ........ A61B 18/1492 606/41 |
| 2012/0157993 | A1* | 6/2012 | Jenson ............... A61B 18/1492 606/41 |
| 2012/0197246 | A1* | 8/2012 | Mauch ............... A61B 18/1492 606/33 |
| 2012/0323174 | A1* | 12/2012 | Shih ............... A61B 18/1492 604/95.04 |
| 2013/0006238 | A1* | 1/2013 | Ditter ............... A61B 5/0538 606/41 |
| 2014/0031812 | A1 | 1/2014 | Brannan et al. |
| 2014/0088586 | A1 | 3/2014 | Davis et al. |

FOREIGN PATENT DOCUMENTS

| | | |
|---|---|---|
| JP | H 04-061840 A | 2/1992 |
| JP | H 05-76482 | 10/1993 |
| JP | H 07-323091 A | 12/1995 |
| JP | H 11-239564 A | 9/1999 |
| JP | 2000-233027 A | 8/2000 |
| JP | 2014-171885 A | 9/2014 |
| JP | 2014-193240 A | 10/2014 |
| JP | 2016-112422 A | 6/2016 |

OTHER PUBLICATIONS

English Translation of Japanese Search Report for Application No. JP 2015-244974, dated Oct. 17, 2019, 13 pages.
English Translation of Japanese Notification of Reasons for Refusal for Application No. JP 2020-138487, dated Jun. 22, 2021, 4 pages.
English Translation of Japanese Notice of Reasons for Refusal for Application No. JP 2015-244974, dated Oct. 29, 2019, 6 pages.
English Translation of Japanese Written Opinion for Application No. JP 2015-244974, dated Jan. 24, 2020, 4 pages.
English Translation of Japanese Decision of Refusal for Application No. JP 2015-244974, dated Apr. 21, 2020, 4 pages.
English Translation of Chinese First Office Action for Application No. CN 201510947379.1, dated Aug. 2, 2019, 6 pages.
English Translation of Chinese Second Office Action for Application No. CN 201510947379.1, dated Jul. 14, 2020, 6 pages.
English Translation of Chinese Third Office Action for Application No. CN 201510947379.1, dated May 10, 2021, 8 pages.
First Search Report for Chinese Patent Application No. 201510947379.1, 2 pages.
Supplementary Search Report for Chinese Patent Application No. 201510947379.1, 3 pages.
English Translation of Japanese Search Report for Application No. JP 2020-138487, dated Jun. 18, 2021, 7 pages.
Australian Examination Report for Application No. AU 2015268762, dated Aug. 7, 2019, 4 pages.
European Communication for Application No. EP 15 200 512.0, dated Apr. 26, 2018, 4 pages.

* cited by examiner

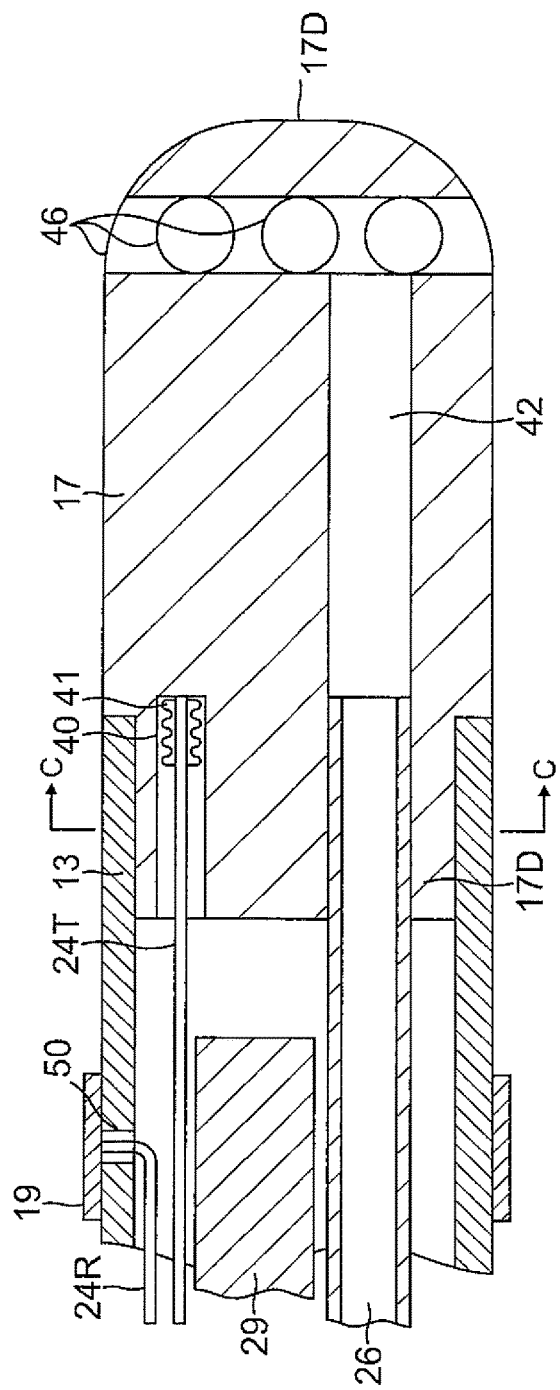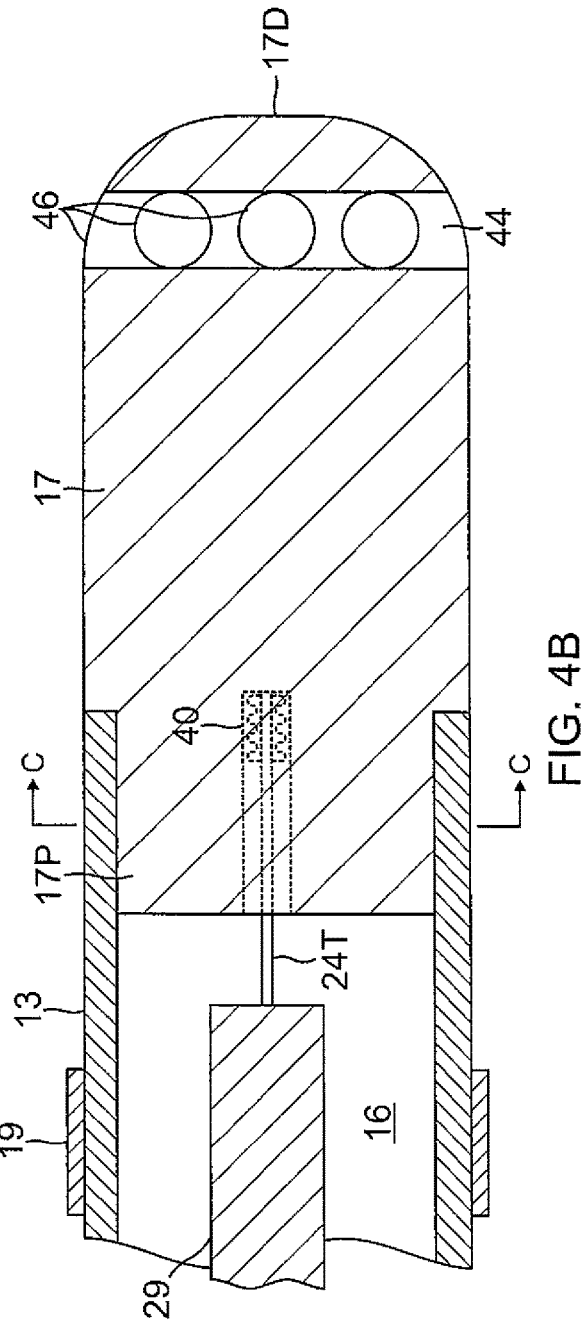

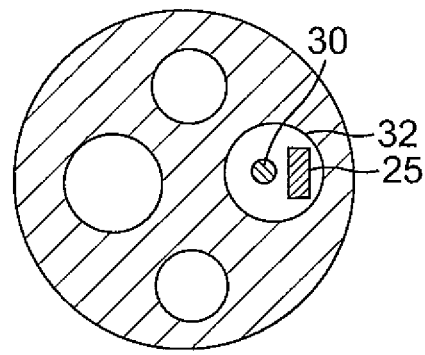
FIG. 7
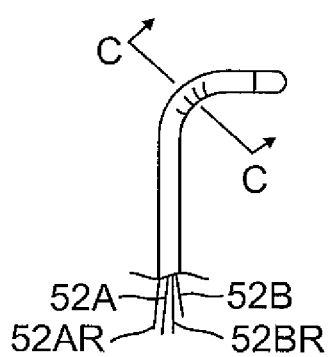 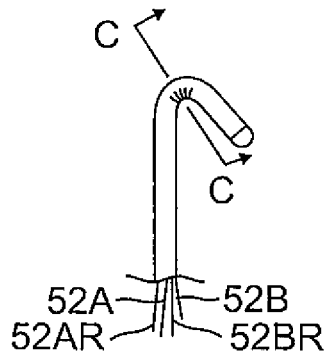 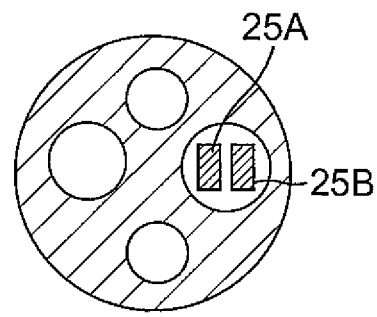
FIG. 8A  FIG. 8B  FIG. 8C
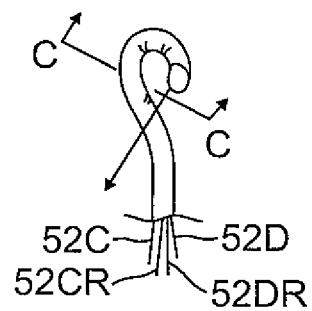 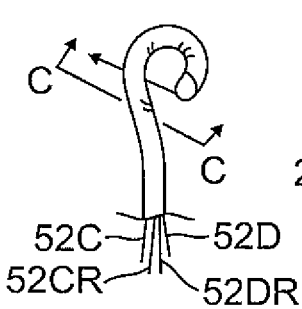 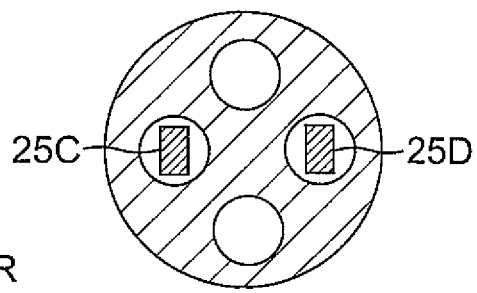
FIG. 9A  FIG. 9B  FIG. 9C

EP CATHETER WITH TRAINED SUPPORT MEMBER, AND RELATED METHODS

FIELD OF INVENTION

This invention relates to medical catheterization. More particularly, this invention relates to steerable and deflectable EP catheters.

BACKGROUND

Medical catheterizations are routinely carried out today. For example, in cases of cardiac arrhythmias, such as atrial fibrillation, which occur when regions of cardiac tissue abnormally conduct electric signals. Procedures for treating arrhythmia include surgically disrupting the origin of the signals causing the arrhythmia, as well as disrupting the conducting pathway for such signals. By selectively ablating cardiac tissue by application of energy, e.g., radiofrequency energy via a catheter, it is sometimes possible to cease or modify the propagation of unwanted electrical signals from one portion of the heart to another. The ablation process destroys the unwanted electrical pathways by formation of non-conducting lesions.

A typical cardiac catheter is inserted through a patient's vascular system into a chamber or vascular structure of the heart. The catheter's distal tip is brought into contact with the heart wall for obtaining electrical and positional information that is processed by a console that includes a processor for generating activation maps, anatomical positional information and other functional images.

More recently, catheter-based ablation has been used in renal denervation. One in four adults suffers from hypertension worldwide. Overactive sympathetic nervous system plays a vital role in pathogenesis of hypertension. Renal denervation has demonstrated exceptional blood pressure reductions in patients with resistant hypertension. In renal catheterization, a very thin catheter is inserted in the groin, passed through the body and into the renal arteries. At the desired location RF or ultrasound energy is activated to deaden the nerves associated with the renal arteries in a way that will effectively switch off one of the mechanisms that cause high blood pressure. These so-called "sympathetic" nerves can be a main cause of hypertension when they become overactive, and by reducing their activity the body responds by lowering heart rate and other factors.

Nitinol wire is often used in the construction of therapeutic and diagnostic catheter distal ends, including geometric distal ends such as a ring, a helix or a basket for use in a chamber or tubular region of the heart where contact with sides of the region is desired. At body temperature, nitinol wire is flexible and elastic and like most metals nitinol wires deform when subjected to minimal force and return to their shape in the absence of that force. Accordingly, a 3-D distal assembly can be easily collapsed to be fed into a guiding sheath, and readily deployed in the chamber or tubular region upon removal of the guiding sheath. Because Nitinol belongs to a class of materials called Shaped Memory Alloys (SMA). These materials have interesting mechanical properties beyond flexibility and elasticity, including shape memory and superelasticity which allow nitinol to have a "memorized shape." That is, nitinol can be trained to remember a particular shape by annealing.

Nitinol has three distinct temperature phases: martensitic phase, austenite phase and annealing phase. The martensitic phase is a low temperature phase where the crystal structure of nitinol is aligned and cubic. The alloy may be bent or formed easily. Bending deforms the crystalline structure of the alloy producing internal stress. In the austenite phase, the nitinol is heated above its transitional temperature where the crystalline structure returns to its non-stress (cubic) state. The transitional temperature of nitinol is highly dependent on the exact nickel and titanium ratio. The transitional temperature of nitinol can be adjusted between about −100 C to +100 C depending on the alloy composition and/or it's processing. Annealing phase is a high temperature phase where the crystalline structure of nitinol can be reoriented to "remember" the shape imposed upon it while it is subjected to the high temperature. The annealing phase for nitinol wire is about 540 degrees Celsius.

Once the memory is established in high temperature annealing, a cooled nitinol wire can be bent out of the memorized shape, whereupon subsequent heating of the nitinol wire above its transition temperature will return it to its memorized shape. Nitinol is activated for such thermal movement at its transition temperature which is typically about 70 degrees Celsius. An electric current may be passed through a Nitinol wire to heat it electrically as the wire's resistance is about 2.5 ohm/m.

The human heart has four chambers and tubular regions feeding into and out of those chambers. A cardiac EP catheter is typically inserted into the vasculature through an incision in a femoral vein of the patient and advanced through the superior vena cava which feeds into the right atrium of the heart. The distal end of the cardiac catheter may then remain in the right atrium, or be further advanced into another chamber and/or a tubular region. The cardiac EP catheter is steered and deflected into each these regions by means of one or more puller wires responsive to a catheter control handle. Cardiac catheters offer a variety of deflection curvatures, as shown in FIG. 11, where each curvature typically has a uniform curvature (forming the arc of a circle of a different radius). Similarly, the renal arteries are accessed through an incision in a femoral artery and a renal catheter is advanced through the aorta to reach the renal arteries. However, unlike the right atrium which is a cavernous region accessed from the relatively wide superior vena cava, the left and right renal arteries are narrower than the aorta and nearly perpendicular to it, making the approach more challenging for a renal catheter.

Accordingly there is a desire for a catheter to be more easily maneuverable in tight spaces and tubular regions, including an EP catheter that can be steerable through a narrow tubular region with a sharp turn. There is also a desire for an EP catheter that can be advanced atraumatically through a patient's vasculature, predictably adopt a preformed shape or configuration upon actuation, and return to an atraumatic configuration for relocation or withdrawal from the patient's body. There is a further desire that such preformed shape or configuration be more acute and/or sharper than configurations previously achieved through one or more puller wires.

SUMMARY OF THE INVENTION

The present invention is directed to a catheter having an elongated body, a deflection section having a support member adapted for heat activation to assume a trained configuration, and a lead wire configured to deliver a current to the support member for heat activation.

In some embodiments, the support member is constructed of a shaped memory alloy, for example, nitinol, and the lead wire is adapted to directly heat the support member. Moreover, the catheter may include a thermally insulating layer covering at least a portion of the support member.

In some embodiments, the trained configuration of the support member extends in a single dimension, in two dimensions or in three dimensions.

In some embodiments, the catheter includes a second support member adapted for heat activation to assume a second trained configuration, wherein the second support member has at least a portion that is distal of the first support member and/or wherein the second support member has a least a portion that is coextensive with the first support member along the longitudinal axis. A second lead wire is provided configured to deliver a current to the second support member.

The present invention also includes a method of using the above catheter, comprising advancing the elongated body and deflection section of the catheter into a patient's vasculature and activating the lead wire to heat the support member to at least its transitional temperature. The method may include allowing the support member to cool to below its transitional temperature before relocating the catheter or removing the catheter from the patient's vasculature. Allowing the support member to cool may include deactivating the lead wire from delivering the current to the support member.

The present invention further includes a method of manufacturing the above catheter, comprising heating the support member to its annealing phase and forming the support member while in its annealing phase into a first configuration, and cooling the support member to below its transitional temperature and forming the support member into a second configuration. In some embodiments, the heating and cooling are prior to assembling the catheter.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 4A is a side cross-sectional view of the distal section of the catheter of FIG. 1, taken along the first diameter.

FIG. 4B is a side cross-sectional view of the distal section of the catheter of FIG. 1, taken along the second diameter generally perpendicular to the first diameter.

FIG. 7 is an end cross-sectional view of an intermediate deflection section, in accordance with an embodiment of the present invention.

FIG. 8A is a side view of a portion of a catheter deflected in one configuration, in accordance with an embodiment of the present invention.

FIG. 8B is a side view of the catheter portion of FIG. 8A deflected in another configuration.

FIG. 8C is an end cross-sectional view of the catheter portion of FIGS. 8A and 8B, taken along line C-C.

FIG. 9A is a side view of a portion of a catheter deflected in one configuration, in accordance with an embodiment of the present invention.

FIG. 9B is a side view of the catheter portion of FIG. 9A deflected in another configuration.

FIG. 9C is an end cross-sectional view of the catheter portion of FIGS. 9A and 9B, taken along line C-C.

DETAILED DESCRIPTION OF THE INVENTION

Figure 1:
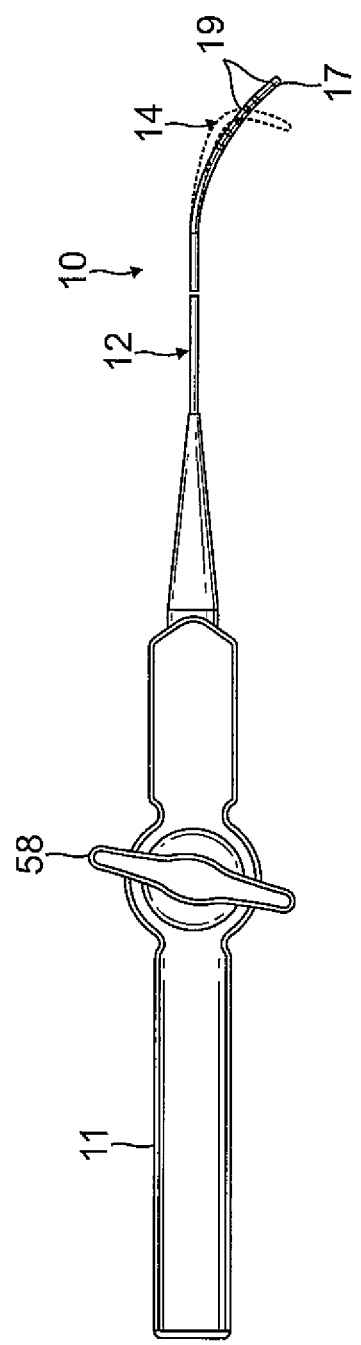
FIG. 1 is a top plan view of a catheter of the present invention, in accordance with an embodiment.

Referring to FIG. 1, a catheter 10 according to the disclosed embodiments comprises an elongated body that may include an insertion shaft or catheter body 12 having a longitudinal axis, and an intermediate deflection section 14 distal of the catheter body that can be deflected off axis from the catheter body longitudinal axis. A distal section 15 extending distally from the intermediate section 14 includes a distal tip electrode 17 and one or more ring electrodes 19. A control handle 11 extends from a proximal end of the catheter body 12. In accordance with a feature of the present invention, the deflection section 14 is constructed with a support member having a temperature-sensitive trained shape which can be heat activated to change from one configuration into another configuration, and be returned to the prior configuration or shaped into another configuration when cooled.

Figure 2A:
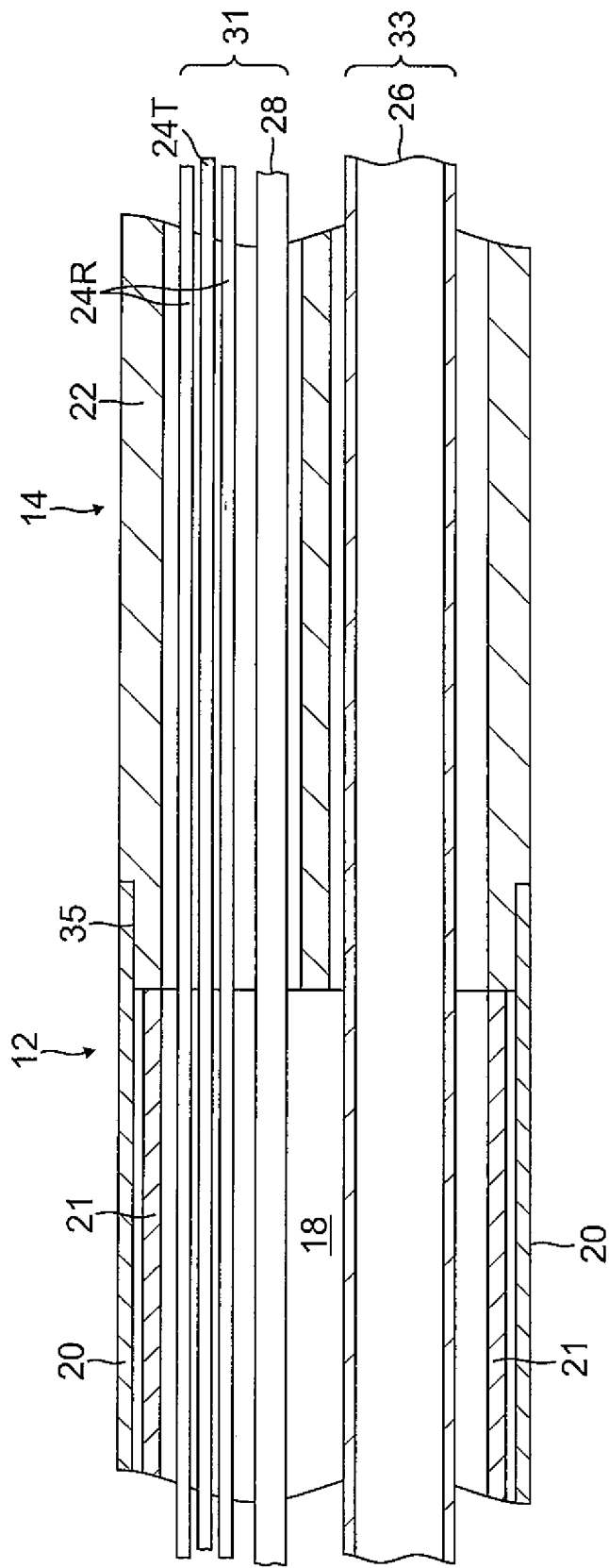
FIG. 2A is a side cross-sectional view of the catheter of FIG. 1, including a junction of a catheter body and an intermediate deflection section, taken along a first diameter.
Figure 2B:
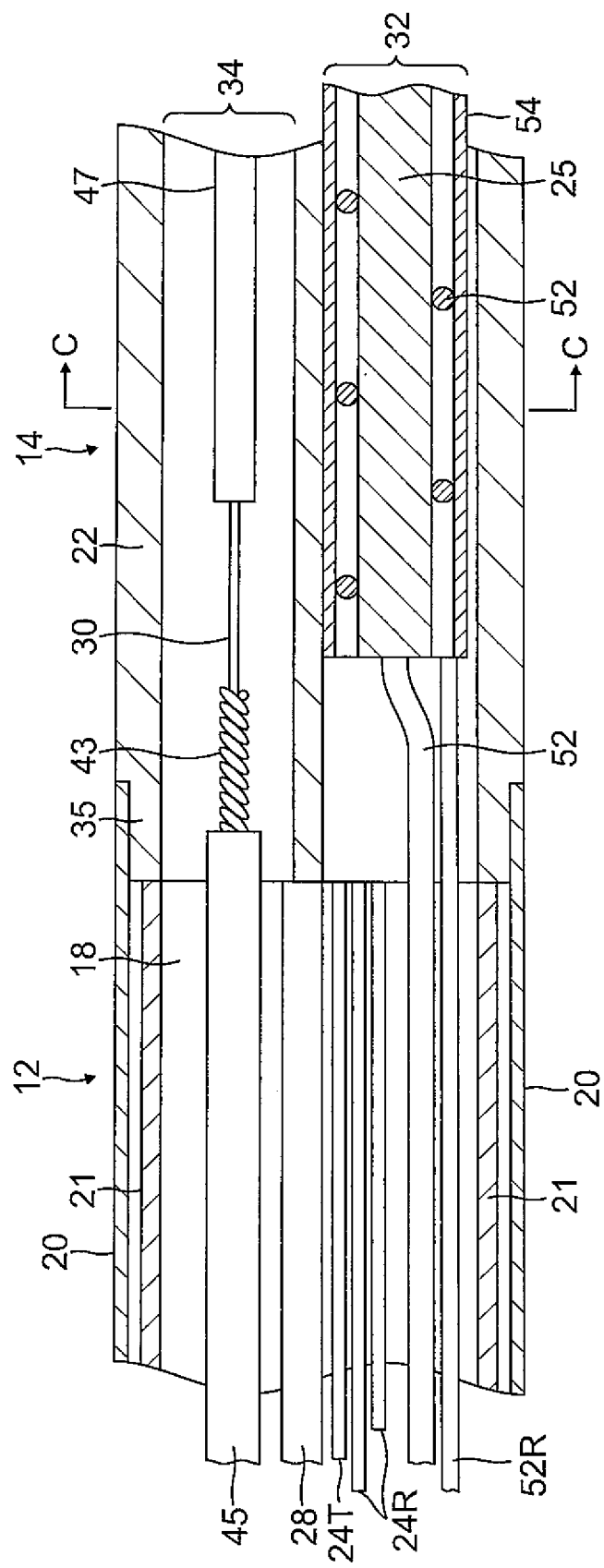
FIG. 2B is a side cross-sectional view of the catheter of FIG. 1, including a junction of a catheter body and an intermediate deflection section, taken along a second diameter generally perpendicular to the first diameter.

In the depicted embodiment of FIGS. 2A and 2B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an imbedded braided mesh of stainless steel or the like, as is generally known in the art, to increase torsional stiffness of the catheter body 12 so that, when the control handle 16 is rotated, the intermediate section 14 will rotate in a corresponding manner.

The outer diameter of the catheter body 12 is not critical, but is preferably no more than about 8 french, more preferably 7 french. Likewise the thickness of the outer wall 20 is not critical, but is thin enough so that the central lumen 18 can accommodate any desired wires, cables and/or tubes. The inner surface of the outer wall 20 is lined with a stiffening tube 21 to provide improved torsional stability. The outer diameter of the stiffening tube 21 is about the same as or slightly smaller than the inner diameter of the outer wall 20. The stiffening tube 21 can be made of any suitable material, such as polyimide, which provides very good stiffness and does not soften at body temperature.

Figure 2C:
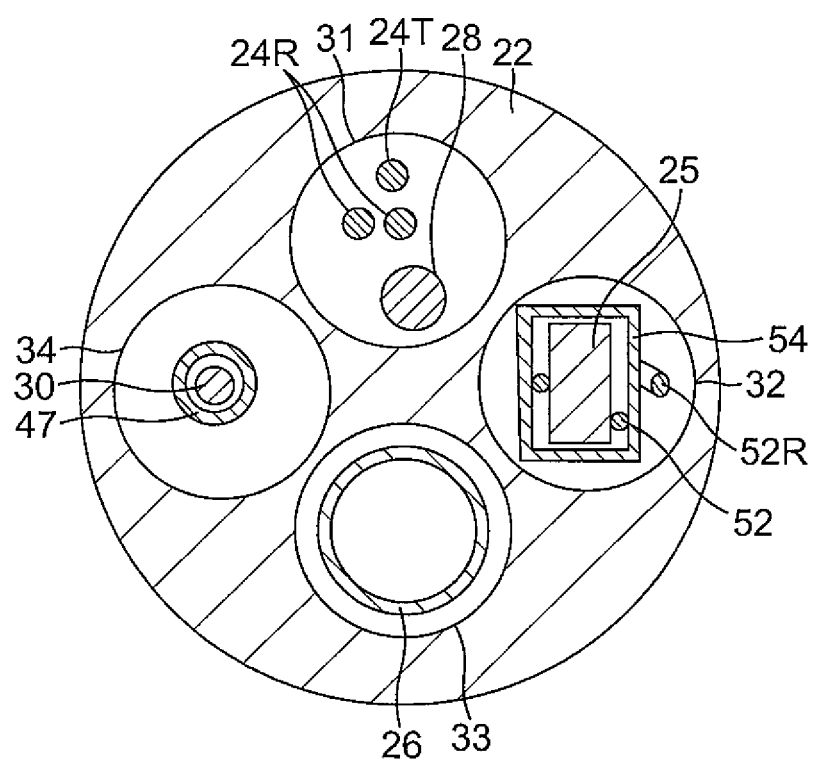
FIG. 2C is an end cross-sectional view of the intermediate deflection section of FIGS. 2A and 2B, taken along line C-C.

With reference to FIGS. 2A, 2B and 2C, the deflectable intermediate section 14 comprises a short section of tubing 22 having multiple lumens, each occupied by the various components extending through the intermediate section 14 from the catheter body 12. In the illustrated embodiment, there are at least four off-axis lumens. Electrode lead 24 wires pass through a first lumen 31. An elongated support member 25 with shape memory passes through a second lumen 32. An irrigation tubing 26 for delivering irrigation fluid to the distal tip electrode 17 passes through a third lumen 34. A cable 28 connected to a distal location sensor 29 (see FIGS. 3A and 3B) passes through the first lumen 31. A puller wire 30 may pass through a fourth lumen 34 to provide the deflection section 14.

The multi-lumened tubing 22 of the intermediate section 14 is made of a suitable non-toxic material that is preferably more flexible than the catheter body 12. A suitable material is braided polyurethane or PEBAX, i.e., polyurethane or PEBAX with an embedded mesh of braided stainless steel or the like. The plurality and size of each lumen are not critical, provided there is sufficient room to house the components extending therethrough. Position of each lumen is also not critical, except the position of the second and fourth lumens 32 and 34 being off-axis, as it is understood that deflections produced by the support member 25 and the puller wire 30 are toward the respective side of the tubing 22 along which each of these respective components extends. Thus, in some embodiments, the catheter is afforded opposite, bi-directional deflection where the support member 25 and the puller wire 30 are situated in diametrically-opposite lumens 32 and 34.

The useful length of the catheter, i.e., that portion that can be inserted into the patient's body can vary as desired. Preferably the useful length ranges from about 60 cm to about 95 cm. The length of the intermediate section 14 is a relatively small portion of the useful length, and preferably ranges from about 2 cm to about 10 cm, more preferably from about 5 cm to about 7 cm.

A means for attaching the catheter body 12 to the intermediate section 14 is illustrated in FIGS. 2A and 2B. The proximal end of the intermediate section 14 comprises an outer circumferential notch 35 that receives the inner surface of the outer wall 20 of the catheter body 12. The intermediate section 14 and catheter body 12 are attached by glue or the like, for example, polyurethane. If desired, a spacer (not shown) can be provided within the catheter body 12 between the distal end of the stiffening tube 21 and the proximal end of the intermediate section 14 to provide a transition in flexibility at the junction of the catheter body 12 and the intermediate section, which allows the junction to bend smoothly without folding or kinking. An example of such a spacer is described in more detail in U.S. Pat. No. 5,964,757, the disclosure of which is incorporated herein by reference.

Figure 3A:
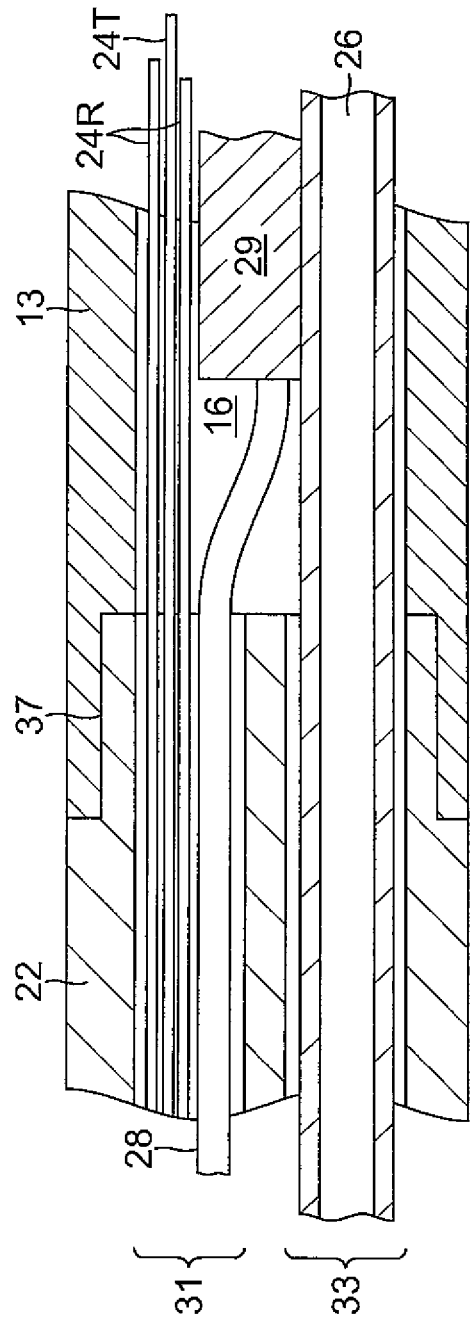
FIG. 3A is a side cross-section view of the catheter of FIG. 1, including a junction of an intermediate deflection section and a distal section, taken along the first diameter.
Figure 3B:
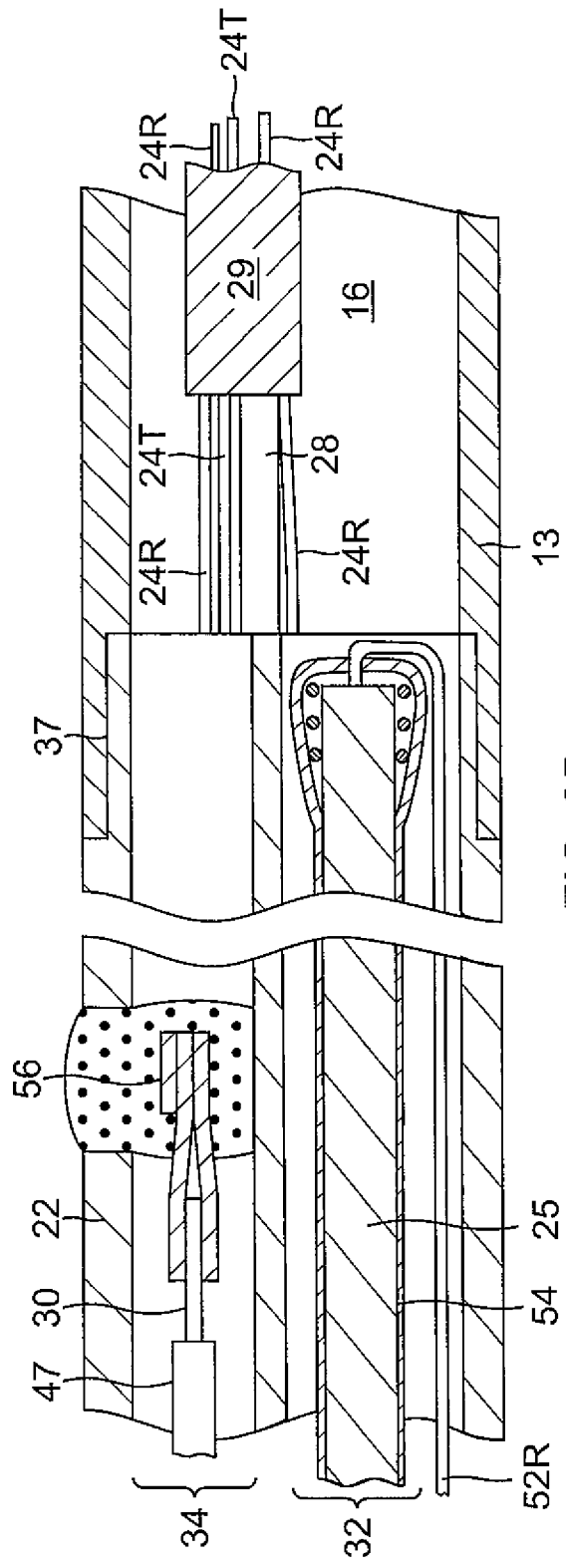
FIG. 3B is a side cross-sectional view of the catheter of FIG. 1, including a junction of an intermediate section and a distal section, taken along the second diameter generally perpendicular to the first diameter.

Distal the intermediate section 14 is the distal section 15. As shown in FIGS. 3A and 3B, the distal section 15 includes a short section of tubing 13, having a central lumen 16, extending between a distal end of the tubing 22 and the distal tip electrode 17. The tubing 13 houses the EM location sensor 29. Extending through the central lumen 16 are lead wire 24T for the distal tip electrode 17, lead wires 24R for the ring electrodes 19, and the irrigation tubing 26.

A means for attaching the tubing 13 to the tubing 22 of the intermediate section 14 is illustrated in FIGS. 3A and 3B. The distal end of the intermediate section 14 comprises an outer circumferential notch 37 that receives an inner circumferential notch of the proximal end of the tubing 13. The tubing 22 and the tubing 13 are attached by glue or the like, for example, polyurethane.

Figure 4C:
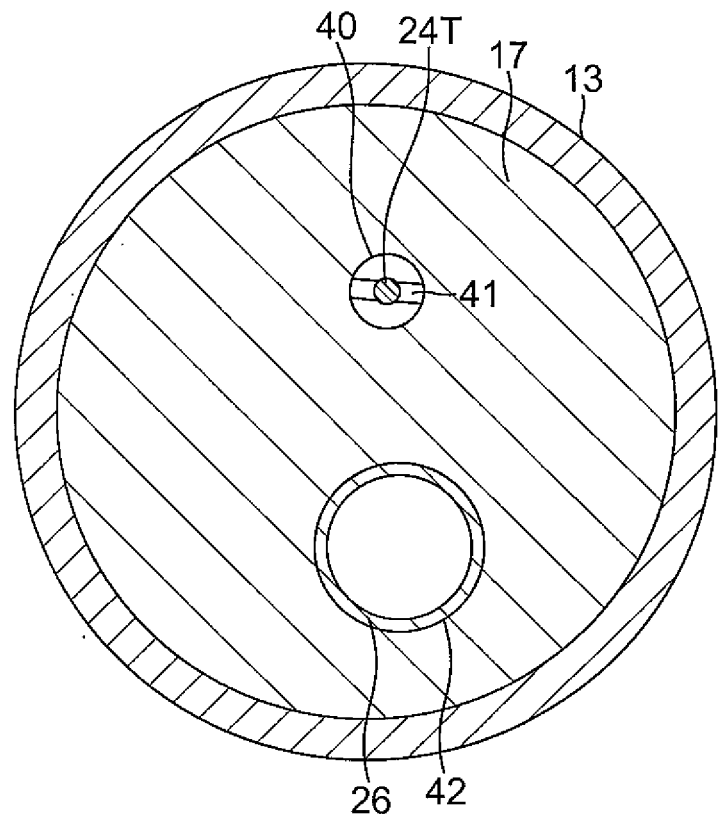
FIG. 4C is an end cross-sectional view of the distal section of FIGS. 4A and 4B, taken along line C-C.

With reference to FIGS. 4A, 4B and 4C, the distal tip electrode 17 has a generally solid cylindrical body with a proximal stem 17P and an atraumatic distal end 17D. The proximal stem 17P is received in a distal end of the tubing 13. A proximal face of the body has a blind hole 40 that receives a distal end of the lead wire 24T anchored in the blind hole 40 by a crimped ferrule 41. In some embodiments, the proximal face also has a longitudinal fluid passage 42 that receives a distal end of the irrigation tubing 26 through which fluid can flow from a fluid source (not shown), along the length of the catheter into the tip electrode 17 and exit the tip electrode 17 via fluid ports 46 and transverse fluid branches 44 that communicate with the longitudinal fluid passage 42.

In some embodiments, ring electrodes 19 are affixed to the outer surface of the connector tubing 13 as shown in FIGS. 4A and 4B. As understood by one of ordinary skill in the art, lead wires 24R are connected to the ring electrodes 19 via holes 50 (FIG. 4A) formed in the side wall of the tubing 13.

In the depicted embodiment, the support member 25 extends through the second lumen 32 of the tubing 22 to define one or more shapes of the intermediate deflection section 14. The support member 25 is made of a material that is flexible and elastic, i.e., that can be straightened or bent out of its original shape upon exertion of a force and is capable of substantially returning to its original shape upon removal of the force. In accordance with a feature of the present invention, a suitable material for construction of the support member 25 also has temperature sensitivity in that the shapes or configurations the support member can assume depend on temperature of the support member. Accordingly, a suitable material for the support member 25 are Shaped Memory Alloys (SMA). These materials have interesting mechanical properties including shape memory and super-elasticity which allow the support member 25 to have a "memorized shape." That is, the support member 25 has been trained to remember a particular shape by an annealing process.

Figure 5:
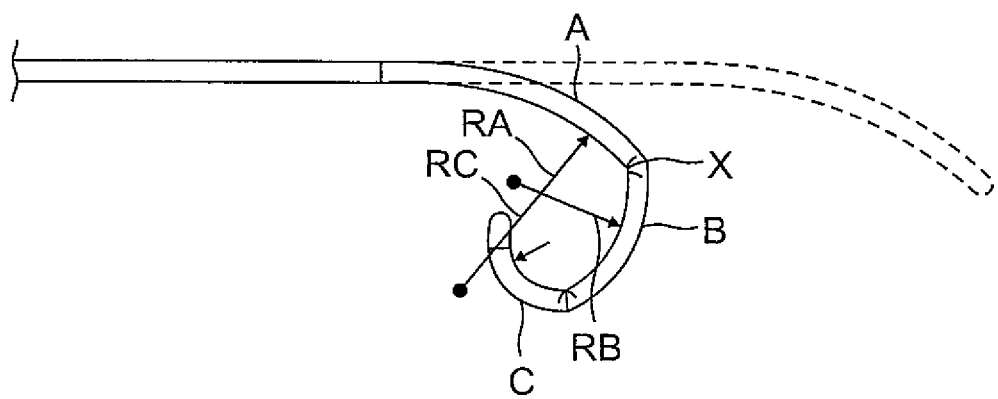
FIG. 5 is a perspective view of a catheter portion in a first configuration (in solid lines) and a second configuration (in broken lines), in accordance with an embodiment of the present invention.

In accordance with a feature of the present invention, the support member 25 has been arranged in a first configuration, for example, as shown in solid lines FIG. 5, and trained to remember the first configuration by high-temperature heating in the annealing phase. When the support member 25 is thereafter cooled to room temperature (about 70 F or 21 C), the support member is in the martensitic phase whereupon it is shaped into a second configuration, for example, as shown in broken lines in FIG. 5. When the support member 25 is subsequently heated to its transitional temperature (for example between about 158 F to 266 F or 70 C to 130 C), the support member 25 is in the austenite phase whereupon it generally returns to the first configuration trained in the annealing phase, for example, as shown in solid lines in FIG. 5. When the heating is terminated, the support member 25 can cool to below its transitional temperature where it can be reshaped.

In some embodiments, the first "trained" configuration includes at least a bend X that is sharp or acute or at least a bend that has multiple different curvatures A, B, and C (each tracing an arc of a circle with a different radius RA, RB and RC), such that the overall curvature is not uniform along its length. The second configuration (in broken lines in FIG. 5) may be a straight or more linear configuration, or a generally linear configuration with a light curvature. Trained configurations may also include 2-D configurations such as zig-zags or "S" and 3-D configurations such as spirals and helices.

A suitable material includes nickel/titanium alloys. Such alloys typically comprise about 55% nickel and 45% titanium, but may comprise from about 54% to about 57% nickel with the balance being titanium. A suitable nickel/titanium alloy is Nitinol, which has excellent shape memory, together with ductility, strength, corrosion resistance, electrical resistivity and temperature stability.

The support member 50 has a cross-section of a predetermined shape that may be generally circular or generally rectangular, including a square shape. It is understood that a generally rectangular cross section can provide greater stiffness compared to a circular cross-section of a comparable size.

To heat the support member 25 into annealing phase, a lead wire 52, e.g., copper wire, is electrically connected to the support member 25, for example, wrapped around a proximal portion of the support member 25, as shown in FIG. 2B. The lead wire 52 extends proximally from the support member 25 through the central lumen 18 of the catheter body 12, and into the control handle 11 where it is connected to an electrical pin connector at the proximal end of the control handle, through which a current can be delivered from a remote power supply (not shown) to heat the support member 25 by resistive heating. To complete the circuit, a return lead wire 52R is electrically connected to the support member 25, for example, wrapped around a distal portion of the support member 25, as shown in FIG. 3B, and extends proximally through the lumen 32 of the tubing 22 and the lumen 18 of the catheter body 12, and into the control handle 11 where it is connected to the electrical pin connector. The support member 25 can be surrounded and covered by a thermally-insulating shrink sleeve 54 that extends along the length of the support member 25 to protect the catheter and the patient from excessive heat.

Figure 6:
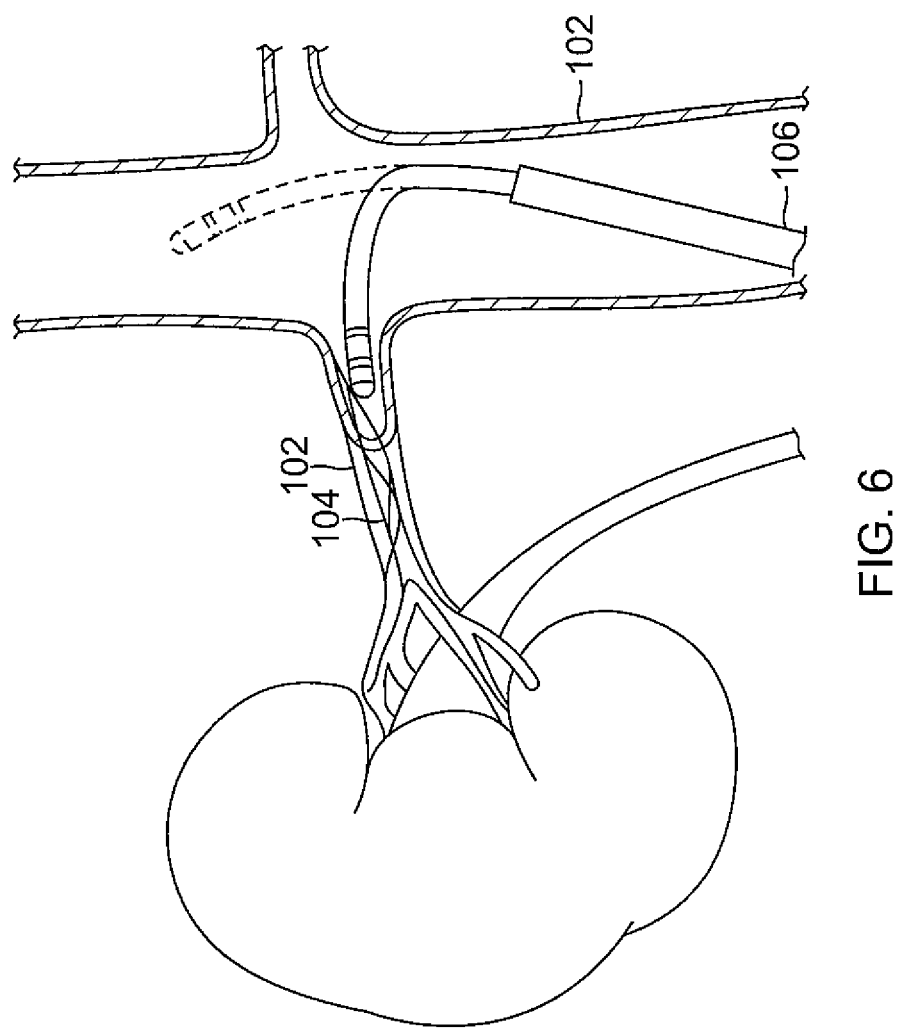
FIG. 6 is a schematic illustration of a catheter of the present invention in use in a renal region, in accordance with an embodiment.

FIG. 6 illustrates a catheter 10 of the present invention in use in a renal artery 100 accessed via the aorta 102. In accordance with a feature of the present invention, the catheter has a shape memory support member 25 that assumes a first or "trained" configuration (in solid lines) when it is above its transitional temperature, and can be flexible and shaped into a second configuration (in broken lines) when it is below its transitional temperature.

At room temperature with the support member 25 having been flexibly shaped into the second configuration (in broken lines), the catheter 10 is advanced atraumatically by an EP professional in a patient through an incision in a femoral artery (not shown). The catheter 10 is fed through a guiding sheath 106 whose distal end is positioned in the lower aorta 102 near the renal artery 100. When the distal section 15 and the intermediate section 14 are near the renal artery 100, the guiding sheath 106 is withdrawn to expose the distal section 15 and the intermediate section 14, with the support member in its second configuration (in broken lines).

To enter the renal artery 100, the EP professional actuates a power supply (not shown) to deliver a current via the lead wire 52 to heat the support 25 to above its transitional temperature. Heated to above its transitional temperature, the support member 25 assumes its first or "trained" configuration (in solid lines) and sharply deflects the intermediate section 14 enabling the distal tip section 15 to readily enter the narrow renal artery 102 so that the distal tip electrode 17 can contact a renal nerve 104. The sharp deflection of the intermediate section 14 provided by the support member 25 may be tempered or accentuated by the puller wire 30 as controlled by the EP professional via the deflection knob 58 (FIG. 1) on the control handle 11.

When the EP professional is ready to relocate or remove the catheter from the renal region, the current to the lead wire 52 is discontinued and the support member 25 is cooled by surrounding blood flow to below its transitional temperature, whereupon the support member 25 is again flexible and (re)shapeable into the second configuration or another configuration and thus can be readily relocated or drawn proximally through the guiding sheath 106 to exit the patient's vasculature.

It is understood that the support member 25 may be imparted with an endless variety of first and second configurations depending on the desire and need. Each of the first and second (or trained and subsequent) configurations may be a 1-D, 2-D or 3-D configuration. It is also understood that the first and second configurations may be tempered, accentuated, adjusted, varied, or even opposed or restricted, as needed or desired by the puller wire 30 extending through the fourth lumen 34. The puller wire is actuated by the deflection knob 58 on the control handle 11 and has a distal end anchored at a predetermined location in the sidewall of the tubing 22 of the intermediate section 14, for example, by a T-bar 56, as shown in FIG. 3B. Depending on the desired interaction between the puller wire 30 and the support member 25, the location of the distal end can be varied relative to the position of the support member 25. In some embodiments, the location may be proximal of the distal end of the support member 25, distal of the distal end of the support member 25, or along the length of the support member 25.

In alternate embodiments, the support member 25 and the puller wire 30 may both pass through a common lumen in the tubing 22 of the intermediate section 14, as shown in FIG. 7, especially where the interaction of these components is intended to be complementary rather than in opposition.

The portion of the puller wire 30 throughout the catheter body 12 is surrounded by a compression coil 43 which has a distal end near the junction of the catheter body 12 and the intermediate deflection section 14, as shown in FIG. 2B. The compression coil 43 is made of any suitable metal, preferably stainless steel, and is tightly wound on itself to provide flexibility, i.e., bending, but to resist compression. The inner diameter of the compression coil is preferably slightly larger than the diameter of the puller wire 30. The outer surface of the compression coil is covered by a flexible, non-conductive sheath 45, e.g., made of polyimide tubing. The compression coil may be formed of a wire having a square or rectangular cross-sectional area, which may make it less compressible than a compression coil formed from a wire having a circular cross-sectional area. As a result, the compression coil 43 keeps the catheter body 12 from deflecting when the puller wire 30 is drawn proximally as it absorbs more of the compression. The portion of the puller wire 30 extending through the intermediate section 14 is surrounded by a plastic, e.g., Teflon®, puller wire sheath, which prevents the puller wire 30 from cutting into the wall of the tubing 22 of the intermediate section 14 when the intermediate section 14 is deflected.

The present invention also is directed to a catheter with one or more heat-responsive support members, each of which may occupy respective lumens or they may share a common lumen in the tubing 22 of the intermediate section 14, and/or be jointly energized by a common lead wire or separately energized by respective lead wires, to provide different movements and configurations along same or different portions of the catheter.

In FIG. 8C, a catheter includes support members 25A and 25B sharing a common lumen 32 but each having a respective lead wire 52A and 52B and a respective return wire 52AR and 52BR. Support member 25A is trained with one configuration and support member 25B is trained with another configuration. Accordingly, an EP professional can select which configuration for the catheter to assume depending on which support member he activates by heating. FIG. 8A illustrates the catheter when a current is delivered by the lead wire 52A to heat-activate support member 25A into its trained configuration. FIG. 8B illustrates the catheter when a current is delivered by the lead wire 52B to heat-activate support member 25B into its trained configuration. Both support members 25A and 25B have a trained configuration with deflection in generally the same direction.

In FIG. 9C, a catheter includes support members 25C and 25D, each occupying a different lumen and each having a different lead wire 52C and 52D and a different return wire 52CR and 52DR. FIG. 9A illustrates the catheter when a current is delivered by lead wire 25C to heat-activate support member 25C into its trained configuration. FIG. 9B illustrates the catheter when a current is delivered the lead wire 25D to heat-activate support member 25D into its trained configuration. In this illustrated embodiment, the support members 25C and 25D may have trained configurations in generally opposing directions.

Figure 10A:
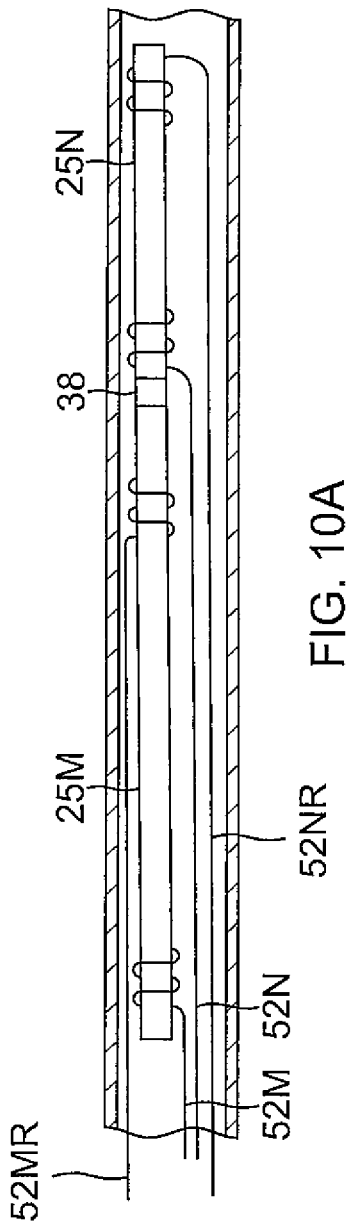
FIG. 10A is a side view of a catheter with parts broken away to reveal serially-connected support members, in accordance with an embodiment of the present invention.
Figure 10B:
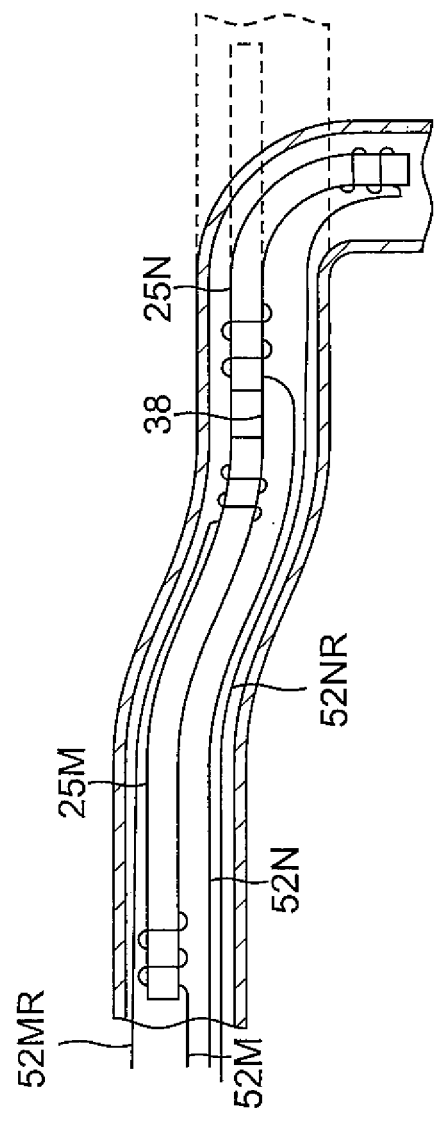
FIG. 10B is a side view of the catheter of FIG. 10A, with the support members in their trained configurations.
Figure 11:
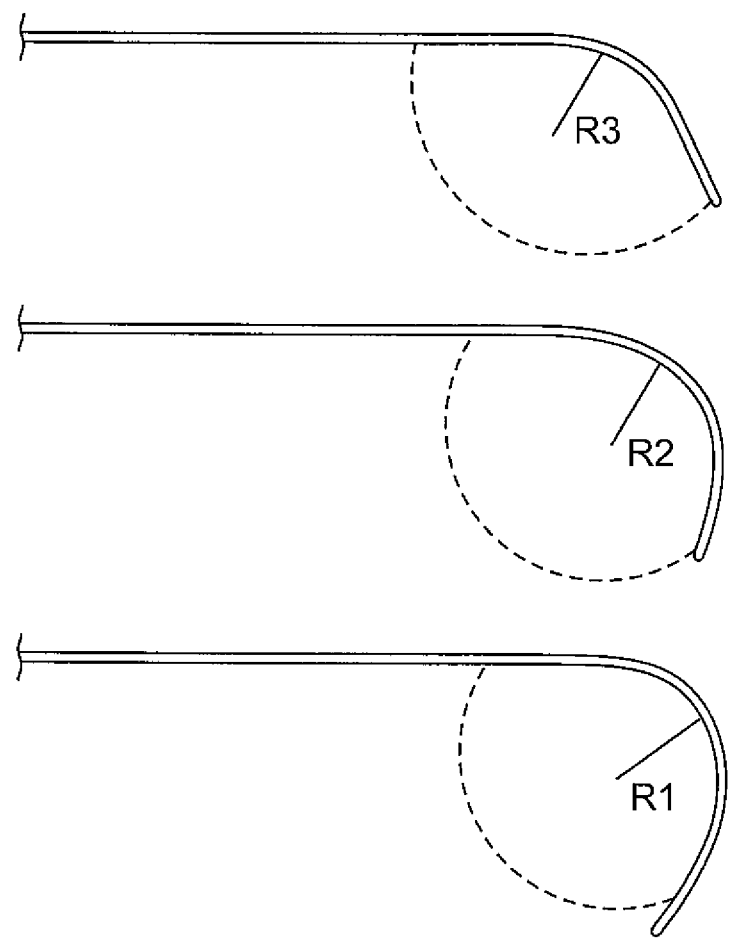
FIG. 11 is a perspective view of catheters in various deflections, as known in the art.

FIG. 10A illustrated a catheter with serially-arranged support members 25M and 25N, each configured for receiving a current by a dedicated lead wire 52M and 52N and a dedicated return wire 52MR and 52NR. A thermally insulating connector 38 extends between and connects the two members. FIG. 10B illustrates the catheter when a current is delivered by lead wire 25M to heat activate support member 25M into is trained configuration, without current being delivered by lead wire 25N which leaves support member 25N unaffected (shown in broken lines). When a current is subsequently delivered to support member 25N, it assumes its trained configuration (shown in solid lines). It is understood that the support members 25M and 25N may be heat activated jointly, or in any time sequence to achieve the desired movement or configuration.

Irrigation fluid is delivered to the distal assembly 17 by the irrigation tubing 43 whose proximal end is attached to a luer hub (not shown) proximal of the control handle 16 and receives fluid delivered by a pump (not shown). The irrigation tubing extends through the control handle 16, the central lumen 18 of the catheter body 12, the third lumen 33 of the intermediate section 14, the central lumen of the tubing 13 and into the fluid passage 42 of the tip electrode 17.

The proximal end of each electrode lead wires 24T and 24R is electrically connected to a suitable connector (not shown) distal of the control handle 11 for transmitting electrical signals from tissue and/or delivery electrical energy to accomplish ablation. The lead wires extend into the control handle 11 and are connected to an electrical connector at a proximal end of the control handle 11.

The catheter of the present invention may be used in any region of anatomy, including the heart and the renal region. Deployed in or near the patient's heart, the catheter is designed to facilitate electrophysiological mapping of a chamber or tubular region of the heart and to transmit energy, e.g., radiofrequency (RF) current, to the catheter electrodes for ablation purposes. For ablation, the catheter is used in conjunction with a multi-channel RF generator and irrigation pump. Deployed in the renal region, the catheter is designed to enter a renal artery to ablate renal nerves.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. Any feature or structure disclosed in some embodiments may be incorporated in lieu of or in addition to other features of any other embodiments, as needed or appropriate. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
an elongated body having a longitudinal axis;
an intermediate section distal the elongated catheter body and comprising a deflectable region, first and second support members extending through at least a portion of the intermediate section and configured for activation to move the deflectable region between a generally straight neutral configuration and a curved configuration, the first and second support members extending through the portion of the intermediate section generally linearly when the deflectable region is in the generally straight neutral configuration, and the curved configuration of the intermediate section imparted by the first and second support members comprises a plurality of different bends such that the curved configuration is not uniform along its length, the plurality of different bends comprising at least first, second and third bends each tracing an arc of a circle with a different radius,
the first support member comprising a first trained curvature of the first support member, and a first neutral configuration of the first support member, the first trained curvature of the first support member comprising at least one of the plurality of different bends in the curved configuration, the first support member being configured for heat activation to move the first support member and thereby the deflectable region to assume the curved configuration of the deflectable region upon heating the first support member above a first transition temperature such that the heat activation of the first support member results in the curved configuration of the deflectable region comprising at least the first trained curvature of the first support member, and the first support member being further configured to return to the first neutral configuration of the first support member upon removal of the heat from the first support member and cooling of the first support member to below the first transition temperature, and
the second support member comprising a second trained curvature of the second support member, and a second neutral configuration of the second support member, the second trained curvature of the second support member being different from the first trained curvature of the first support member and comprising at least one other of the plurality of different bends in the curved configuration, the second support member being configured for heat activation to move the second support member and thereby the deflectable region to assume the curved configuration of the deflectable region upon heating the second support member above a second transition temperature such that the heat activation of the second support member results in the curved configuration of the deflectable region comprising at least the second trained curvature of the second support member, and the second support member being further configured to return to a second neutral configuration of the second support member upon removal of the heat from the second support member and cooling of the second support member to below the second transition temperature;

a first lead wire configured to deliver a current to the first support member;

a second lead wire configured to deliver a current to the second support member;

a puller wire extending through the elongated body and having a distal end anchored in the intermediate section at a position either distal of a distal end of at least one of the first or second support members or between the distal end and a proximal end of at least one of the first or second support members such that when the deflectable region is in the curved configuration, proximal longitudinal movement of the puller wire results in one or more of:
- a more acute bend in the at least one bend of the first trained curvature,
- a less acute bend in the at least one bend of the first trained curvature,
- a more acute bend in the at least one bend of the second trained curvature, or
- a less acute bend in the at least one bend of the second trained curvature;

a tip section distal of the intermediate section and having proximal and distal ends; and a tip electrode configured for direct tissue contact at the distal end of the tip section, the intermediate section comprising a plurality of off-axis lumens, wherein the puller wire and at least one of the first or second support members extending through the intermediate section extend along the length of the intermediate section through a same one of the plurality of off-axis lumens.

2. The catheter of claim 1, wherein the tip electrode comprises an ablation electrode.

3. The catheter of claim 1, wherein each of the first and second support members comprises nitinol.

4. The catheter of claim 1, wherein the first lead wire is configured to heat the first support member, and the second lead wire is configured to heat the second support member.

5. The catheter of claim 1, further comprising a thermally insulating layer covering at least a portion of at least one of the first or second support members.

6. The catheter of claim 1, wherein at least one of the first or second trained curvatures of the curved configuration extends in a single dimension.

7. The catheter of claim 1, wherein at least one of the first or second trained curvatures of the curved configuration extends in two dimensions.

8. The catheter of claim 1, wherein at least one of the first or second trained curvatures of the curved configuration extends in three dimensions.

9. The catheter of claim 1, wherein the second support member has at least a portion that is distal of the first support member.

10. The catheter of claim 1, wherein the second support member has at least a portion that is coextensive with the first support member along the longitudinal axis of the elongated body.

11. A method of using the catheter of claim 1, comprising:
advancing the elongated body and intermediate section of the catheter into a patient's vasculature; and
activating at least one of the first and second lead wires to heat a respective one of the first and second support members to at least a respective one of the first and second transitional temperatures.

12. The method of claim 11, further comprising:
allowing the respective one of the first or second support member to cool to below the respective one of the first or second transitional temperature; and
removing the catheter from the patient's vasculature.

13. The method of claim 12, wherein the allowing the respective one of the first or second support member to cool includes deactivating the respective one of the first or second lead wire.

14. A method of manufacturing a catheter of claim 1, comprising:
heating each of the first and second support members to its respective annealing phase and forming each of the first and second support members while in its respective annealing phase into the respective first or second trained curvatures; and
cooling each of the first and second support members to below its respective transitional temperature and forming the respective first or second support member into the respective first or second neutral configuration.

15. The catheter of claim 1, wherein the first and second support members are serially arranged such that the proximal end of the second support member is distal of and spaced apart from the distal end of the first support member.

16. The catheter of claim 15, further comprising a thermally insulating connector extending between the distal end of the first support member and the proximal end of the second support member and connecting the first and second support members.

17. The catheter of claim 1, wherein the puller wire and the at least one of the first or second support members extending through the same off-axis lumen in the intermediate section are anchored at their distal ends within the same off-axis lumen.

18. A catheter comprising:
an elongated body having a longitudinal axis;
an intermediate section distal the elongated catheter body and comprising a deflectable region, first and second support members extending through at least a portion of the intermediate section and configured for activation to move the deflectable region between a generally straight neutral configuration and a curved configuration, the first and second support members extending through the portion of the intermediate section generally linearly when the deflectable region is in the generally straight neutral configuration, and the curved configuration of the intermediate section imparted by the first and second support members comprises a plurality of different bends such that the curved configuration is not uniform along its length, the plurality of different bends comprising at least first, second and third bends each tracing an arc of a circle with a different radius, the first support member comprising a first trained curvature of the first support member, and a first neutral configuration of the first support member, the first trained curvature comprising at least one of the plurality of different bends in the curved configuration, the first support member being configured for heat activation to move the first support member and thereby the deflectable region to assume the curved configuration of the deflectable region upon heating the first support member above a first transition temperature such that the heat activation of the first support member results in the curved configuration of the deflectable region comprising at least the first trained curvature of the first support member, and the first support member being further configured to return to the first neutral configuration of the first support member upon removal of the heat from the first support member and cooling of the first support member to below the first transition temperature, and the second support member comprising a second trained curvature of the second support member, and a second neutral configuration of the second support member, the second trained curvature of the second support member being different from the first trained curvature of the first support member and comprising at least one other of the different bends in the curved configuration, the second support member being configured for heat activation to move the second support member and thereby the deflectable region to assume the curved configuration of the deflectable region upon heating the second support member above a second transition temperature such that the heat activation of the second support member results in the curved configuration of the deflectable region comprising at least the second trained curvature of the second support member and the second support member being further configured to return to the second neutral configuration of the second support member upon removal of the heat from the second support member and cooling of the second support member to below the second transition temperature;

a lead wire configured to deliver a current to the first and second support members;

a puller wire extending through the elongated body and having a distal end anchored in the deflectable section at a position either distal of a distal end of at least one of the first or second support members or between the distal end and a proximal end of at least one of the first or second support members such that when the deflectable region is in the curved configuration, proximal longitudinal movement of the puller wire results in one or more of:

a more acute bend in the at least one bend of the first trained curvature, a less acute bend in the at least one bend of the first trained curvature, a more acute bend in the at least one bend of the second trained curvature, or a less acute bend in the at least one bend of the second trained curvature;

a tip section distal of the intermediate section and having proximal and distal ends; and a tip electrode configured for direct tissue contact at the distal end of the tip section, the intermediate section comprising a plurality of off-axis lumens, wherein the puller wire and the at least one of the first or second support members extending through the intermediate section extend through the intermediate section through a same one of the plurality of off-axis lumens.

19. The catheter of claim 18, wherein each of the first and second support members comprises nitinol.

20. The catheter of claim 18, wherein the puller wire and the at least one of the first or second support members extending through the same off-axis lumen in the intermediate section are anchored at their distal ends within the same off-axis lumen.

* * * * *

UNITED STATES PATENT AND TRADEMARK OFFICE
CERTIFICATE OF CORRECTION

PATENT NO. : 11,628,009 B2
APPLICATION NO. : 14/574246
DATED : April 18, 2023
INVENTOR(S) : Vishav Manak Singh Aujla It is certified that error appears in the above-identified patent and that said Letters Patent is hereby corrected as shown below:

In the Claims

In Column 12, Line 27, in Claim 14, delete "its" and insert -- a --.

Signed and Sealed this
Twenty-seventh Day of June, 2023

Katherine Kelly Vidal
*Director of the United States Patent and Trademark Office*